(12) United States Patent
Soraker et al.

(10) Patent No.: US 9,278,891 B2
(45) Date of Patent: Mar. 8, 2016

(54) APPARATUS AND METHOD FOR CONDUCTING A FISCHER-TROPSCH SYNTHESIS REACTION

(75) Inventors: Pal Soraker, Trondheim (NO); Manfred Ruppel, Dietzenbach (DE); Dag Schanke, Trondheim (NO); Matthias Wagner, Nidderau (DE)

(73) Assignee: GTL.F1 AG, Zurich (CH)

( * ) Notice: Subject to any disclaimer, the term of this patent is extended or adjusted under 35 U.S.C. 154(b) by 715 days.

(21) Appl. No.: 13/140,384

(22) PCT Filed: Dec. 8, 2009

(86) PCT No.: PCT/GB2009/002836
§ 371 (c)(1),
(2), (4) Date: Sep. 6, 2011

(87) PCT Pub. No.: WO2010/072992
PCT Pub. Date: Jul. 1, 2010

(65) Prior Publication Data
US 2011/0313063 A1 Dec. 22, 2011

(30) Foreign Application Priority Data

Dec. 22, 2008 (GB) .................................. 0823361.1

(51) Int. Cl.
*B01J 8/22* (2006.01)
*C10G 2/00* (2006.01)
*C07C 1/04* (2006.01)
*B01J 8/00* (2006.01)

(52) U.S. Cl.
CPC ................ *C07C 1/041* (2013.01); *B01J 8/006* (2013.01); *B01J 8/22* (2013.01); *B01J 8/228* (2013.01); *C10G 2/32* (2013.01); *C10G 2/342* (2013.01); *C10G 2/344* (2013.01)

(58) Field of Classification Search
None
See application file for complete search history.

(56) References Cited

U.S. PATENT DOCUMENTS

| 4,166,840 A | 9/1979 | Chapman |
| 4,595,145 A | 6/1986 | Pratt et al. |
| 4,610,851 A | 9/1986 | Colvert et al. |
| 4,624,968 A | 11/1986 | Kim et al. |
| 5,166,072 A | 11/1992 | Krauling et al. |
| 5,384,336 A | 1/1995 | Koros |

(Continued)

FOREIGN PATENT DOCUMENTS

| CA | 2624815 A1 * | 4/2007 |
| EP | 0592176 | 4/1994 |

(Continued)

OTHER PUBLICATIONS

Twigg, Martyn V., editor, "Catalyst Handbook," 2nd ed., Wolf Publishing Ltd. (1989), p. 195.

(Continued)

*Primary Examiner* — Jennifer A Leung
(74) *Attorney, Agent, or Firm* — Patterson Thuente Pedersen, P.A.

(57) ABSTRACT

A system for a Fischer-Tropsch synthesis using a three-phase reactor in which a primary filter removes coarse catalyst particles from the product and in which catalyst fines are removed in a secondary filter. Some or all portion of the product wax from the secondary filter can be recycled back to the reactor, either as a back flush medium for the primary filter or directly to the slurry in the reactor, whereby removal of catalyst fines is rendered independent of the rate of wax production.

20 Claims, 3 Drawing Sheets

(56) References Cited

U.S. PATENT DOCUMENTS

| | | |
|---|---|---|
| 5,527,473 A | 6/1996 | Ackerman |
| 5,827,903 A | 10/1998 | White et al. |
| 6,160,026 A | 12/2000 | Dai et al. |
| 6,278,034 B1 | 8/2001 | Espinoza et al. |
| 6,835,756 B2 | 12/2004 | Font Freide et al. |
| 2003/0021738 A1 | 1/2003 | Brunard et al. |
| 2003/0050348 A1 | 3/2003 | Kennedy |
| 2003/0195264 A1 | 10/2003 | Newton et al. |
| 2004/0147621 A1 | 7/2004 | Font-Freide et al. |
| 2005/0000861 A1 | 1/2005 | Clerici et al. |
| 2005/0047992 A1 | 3/2005 | Dietrich et al. |
| 2005/0113465 A1 | 5/2005 | O'Rear et al. |
| 2006/0135631 A1 | 6/2006 | Kopponen et al. |
| 2007/0197667 A1* | 8/2007 | Vogel .................... 518/700 |
| 2009/0071337 A1 | 3/2009 | Nieuwoudt |
| 2010/0137458 A1 | 6/2010 | Erling |
| 2011/0313062 A1 | 12/2011 | Ruppel et al. |

FOREIGN PATENT DOCUMENTS

| | | |
|---|---|---|
| EP | 0 609 079 A1 | 8/1994 |
| GB | 1250222 | 10/1971 |
| GB | 1265770 | 3/1972 |
| GB | 2 408 744 A | 6/2005 |
| JP | 5254078 | 5/1977 |
| WO | WO 00/63141 | 10/2000 |
| WO | WO 03/010117 A2 | 2/2003 |
| WO | WO 2004/026994 A1 | 4/2004 |
| WO | WO2004026994 | 4/2004 |
| WO | WO 2005/005038 A1 | 1/2005 |
| WO | WO 2005/094979 | 10/2005 |
| WO | WO 2006/097905 | 9/2006 |
| WO | WO 2007/009952 A1 | 1/2007 |
| WO | WO 2007/041726 A1 | 4/2007 |
| WO | WO 2007/065904 A1 | 6/2007 |
| WO | WO 2007/086612 | 8/2007 |
| WO | WO2008062208 | 5/2008 |
| WO | WO 2008/146239 A2 | 12/2008 |
| WO | WO 2009/043201 | 4/2009 |
| WO | WO 2010/072992 | 7/2010 |

OTHER PUBLICATIONS

International Search Report for International Application No. PCT/GB2007/004484 dated Mar. 25, 2009 and GB Search Report for GB0623394.4 dated Mar. 25, 2007.

International Search Report for International Application No. PCT/GB2009/002698 dated Mar. 26, 2010 and GB Search Report for GB0821094.0 dated Feb. 11, 2009.

International Search Report for International Application No. PCT/GB/2010/001223 dated Mar. 21, 2011.

Application and File History for U.S. Appl. No. 12/515,933, filed Feb. 1, 2010, inventor Rytter.

Application and File History for U.S. Appl. No. 13/130,041, filed Sep. 7, 2011, inventors Ruppel et al.

Steyberg and Dry (Fischer-Tropsch Technology) in studies in Surface Science and Catalysis v. 152 (2004) 700 pages.

International Search Report for International Application No. PCT/GB2011/000596 dated Jun. 30, 2011.

Application and File History for U.S. Appl. No. 13/641,847, filed Oct. 17, 2012.

Koch-Glitsch LP (Koch-Otto York separations technology): Mist Elimination. Jan. 1, 2007. XP002627243, pp. 3,4,9,10, retried Mar. 8, 2011. www.koch-glitsch.com/Document%20Library/ME_ProductCatalog.pdf.

* cited by examiner

APPARATUS AND METHOD FOR CONDUCTING A FISCHER-TROPSCH SYNTHESIS REACTION

RELATED APPLICATIONS

The present application is a National Phase entry of PCT Application No. PCT/GB2009/002836, filed Dec. 8, 2009, which claims priority from Great Britain Application No. 0823361.1, filed Dec. 22, 2008, the disclosures of which are hereby incorporated by reference herein in their entirety.

FIELD OF THE DISCLOSURE

The present invention relates to an apparatus and method for conducting an F-T synthesis reaction and is particularly concerned with maintaining wax filtration flux in a three-phase slurry bubble column reactor (SBCR).

BACKGROUND OF THE DISCLOSURE

In reactors that generate high molecular weight hydrocarbons (wax), some of the reaction products must be removed from the reactor in liquid form, preferably without losing catalyst, which will be in suspension in a finely divided form.

It is well known that there is a high risk of generating fines in a FT slurry reactor due to attrition/erosion of catalyst, and this can create the danger of catalyst loss and blocking of wax filters by fine catalyst particles.

Several methods have been described in the literature for effecting the separation of the catalyst and/or wax from the reactor slurry, such as internal filtration, external filtration, hydrocyclones, magnetic methods and settling/sedimentation. As the concentration of catalyst fines builds up in the reactor slurry, the flux through the filter will decrease and at a certain point it will be too low to maintain the filtrate capacity needed for a given wax production rate.

There are several known ways of reducing the effect of fines on the filtration, such as using a larger filtration area, more frequent cleaning (for example back-flushing) of filters, higher differential pressure for filtration etc. However all of these methods are either space limited or energy consuming and may shorten the life time of the filters.

The relationship between fines concentration in the slurry and the filtration flux is highly non-linear. This is shown as a very large decrease in flux as a result of increasing the fines concentration at very low or virtually zero fines concentrations, while further increases in fines concentration has a smaller effect. The fines generation rate in the reactor is not particularly sensitive to the wax production rate, but is more sensitive to the fluid dynamics of the reactor, which are for example related to the feed gas rates and of course the mechanical properties of the catalyst. Operating the reactor at conditions that give lower wax production is not a permanent solution; it simply extends the operating time somewhat and gives lower overall production. The concentration of fines in the slurry will increase at a higher rate if the removal of wax is decreased as the only outlet of fines is through the filtered wax.

It is therefore important to have a system for controlling the fines removal rate out of the reactor, both during normal operation and during upset conditions/turn down.

SUMMARY OF THE DISCLOSURE

According to one aspect of the invention, there is provided apparatus for conducting a three-phase reaction, in which gaseous reactants are reacted in the presence of a finely divided solid catalyst in suspension in a liquid comprising, at least in part, the reaction product of the gaseous reactants, thereby forming a slurry, the apparatus comprising a reactor vessel, a primary filter unit, and a filtrate cleaning unit, and in which: the reactor vessel includes a reactant inlet and a gas outlet and is arranged to contain the slurry in use; the primary filter unit is arranged to be in contact with slurry in use, the primary filter unit having an outlet for primary filtrate; and the filtrate cleaning unit is arranged to remove further particulate material from the filtrate in use, and includes an inlet for the filtrate, an outlet for liquid product that has been subjected to cleaning; and in which the apparatus further includes a cleaned liquid product recycle line from the filtrate cleaning unit to the reactor.

According to another aspect of the invention, there is provided a process for conducting a three phase reaction in which gaseous reactants are reacted in the presence of a finely divided solid catalyst in suspension in a liquid comprising, at least in part, the reaction product of the gaseous reactants, thereby forming a slurry, the process comprising the steps of: introducing the gaseous reactants into the slurry in a reactor; subjecting the slurry to a filtration step to remove particulate material in a primary filter unit to produce a filtrate stream; subjecting the filtrate stream to a cleaning step in a filtrate cleaning unit thereby removing further particulate material to produce a liquid product stream; and recycling at least a portion of the liquid product stream to the reactor.

Thus, the present invention makes it possible, in a way which is independent of the wax production rate from the reaction, to use some of the filtration capacity in the primary filter to improve the filtration performance by removing fines from the reactor slurry, by using a secondary filter and recycling at least part of this secondary filtrate to the reactor to improve the slurry properties in the reactor to achieve a higher filtration rate in the primary filter.

As the primary filtration capacity is very dependent on the fines concentration in the slurry, it is important to be able to remove fines from the slurry at a higher rate than the generation of fines after an upset that has given a higher fines concentration than the normal steady state concentration in the slurry. By utilizing the primary filtration capacity and the wax polishing capacity to recycle maximum pure wax to the reactor, and, if necessary, operating the reactor at conditions that gives low fines generation, the fines concentration in the slurry can be gradually decreased and thereby achieve increased primary filtration capacity.

Preferably, there is a cleaned liquid product recycle line from the filtrate cleaning unit to the primary filter unit, whereby the primary filter can be back flushed using a portion of the liquid product. Preferably, the filtrate cleaning unit is a secondary filter unit comprising a relatively fine filter.

Thus, an important feature of the invention is that the primary filter removes coarser catalyst particles which are retained within the reactor while the primary filtrate, including fines, is fed to the secondary filter. In the secondary filter or wax polishing unit, the fines are removed and almost particle free wax is produced. The net product is taken from this pure wax, however, if pure wax is recycled to the reactor, the flowrate of liquid product in the form of pure wax from the secondary filter exceeds the rate at which wax is catalytically produced in the reactor. Therefore, crucially, a portion of the product from the secondary filter is recycled to the reactor in order to increase the flow of wax out of the reactor. Part or all of the pure wax from secondary filtration (wax polishing unit) can be used at the same time for backflushing the primary filter as this will also effectively constitute a recycle of pure wax. In this way, the rate of wax product removal from the reactor via the primary filter is not limited by the rate of net removal of product from the system as a whole, the latter being equal to the catalytic production of wax in the reactor.

Preferably, the primary filter is located within the reactor, and is arranged, in use, to be at least partially immersed in the slurry. Preferably, the secondary filter (wax polishing unit) is outside the reactor. The system may include a degasser unit located between the primary and secondary filters, which preferably includes a gas outlet, and outlet for primary filtrate leading to the secondary filter, and an optional recycle line for primary filtrate leading back to the reactor.

There may also be a filtrate buffer unit arranged to receive cleaned liquid product from the filtrate cleaning unit, the filtrate buffer unit having liquid product outlet, a liquid product recycle line to the reactor, and an optional liquid product recycle line to the primary filter unit.

In operation, the back flushing is carried out intermittently, as required, depending upon catalyst particle build-up on the primary filter. The back flushing causes catalyst particles located on the outside of the filter to re-enter the slurry and will also to a certain extent remove particles located within the filter media.

The primary filter is preferably a static filter with a relatively coarse pore size, typically +/−50% of the mean catalyst particle size. Typically, the mean catalyst particle size is in the range 50 to 100 µm. The flow through the primary filter is controlled by the differential pressure over the filter and/or a flow control valve on the primary filtrate line leaving the reactor.

Preferably, the process includes a fines removal step in which fine catalyst particles filtered out in the filtrate cleaning step are removed. This wax polishing step can be a secondary filtration system, for example a cross flow filtration system, disposable cartridges with once through or multi pass or back washable filters, an effective guard bed, or a centrifuge, or any other equipment with a high efficiency for removal of particles remaining in the filtrate from the primary filter unit. It preferably has a high efficiency for removal of particles <25 µm. The catalyst particles from the wax polishing step are preferably not recycled back to the slurry reactor.

By keeping the flux through the internal filters high and independent of the net wax production rate, the fines are removed continuously in the filtrate cleaning system, while the surplus of secondary filtered wax is recycled to the reactor to maintain a constant slurry level and a low concentration of catalyst fines in the slurry. This or part of this wax can then be used for back flushing the primary filters.

Preferably, the process includes a degassing step in which gas is separated from the primary filtrate stream from the primary filter and is removed from the process, while the remaining, liquid phase is directed to the filtrate cleaning or wax polishing unit. Primary filtrate preferably enters into a degassing vessel which is pressure controlled to be able to adjust the differential pressure over the primary filter and thereby also the flux. As an option, this vessel can be used as a settling separation vessel to avoid losing relatively larger catalyst particles, for example particles >50% of mean particle size. Due to their higher sedimentation velocity, the larger particles will tend to settle to the bottom of the degassing vessel. From the bottom of the degassing vessel, primary filtrate including larger catalyst particles can be recycled back to the reactor either by gravity or by pumping.

In the case of the various recycle streams, they may be continuous or intermittent.

Preferably, the reaction is a Fischer-Tropsch synthesis reaction to produce hydrocarbon wax, carried out in a slurry bubble column reactor, and in which the $H_2$ and CO are supplied to a slurry in the reactor, the slurry comprising the catalyst in suspension in a liquid including the reaction products of the $H_2$ and CO, the catalyst being maintained in suspension in the slurry at least partly by the motion of the gas supplied to the slurry. Preferably, the reaction temperature is in the range 190-250° C. and the reaction pressure is in the range 10-60 bar. Preferably, the $H_2/CO$ ratio of the gases supplied to the Fischer-Tropsh synthesis reactor is in the range 1.1 to 2.2 and the superficial gas velocity in the reactor is in the range 5 to 60 cm/s.

The product of the process may be subjected to post-processing steps, such as de-waxing, hydro-isomerisation, hydro-cracking and combinations of these. The invention extends to the product of the process described.

The term 'wax' as used herein means a substance comprising hydrocarbons, which at normal operating temperatures of the reactor is a liquid although the substance may contain varying amounts of hydrocarbons that at ambient temperatures are solid or semisolid (wax-like).

BRIEF DESCRIPTION OF THE FIGURES

The invention may be carried into practice in various ways and one embodiment will now be described in the following Example, with reference to the accompanying drawing in which.

DETAILED DESCRIPTION OF THE FIGURES

Figure 1:
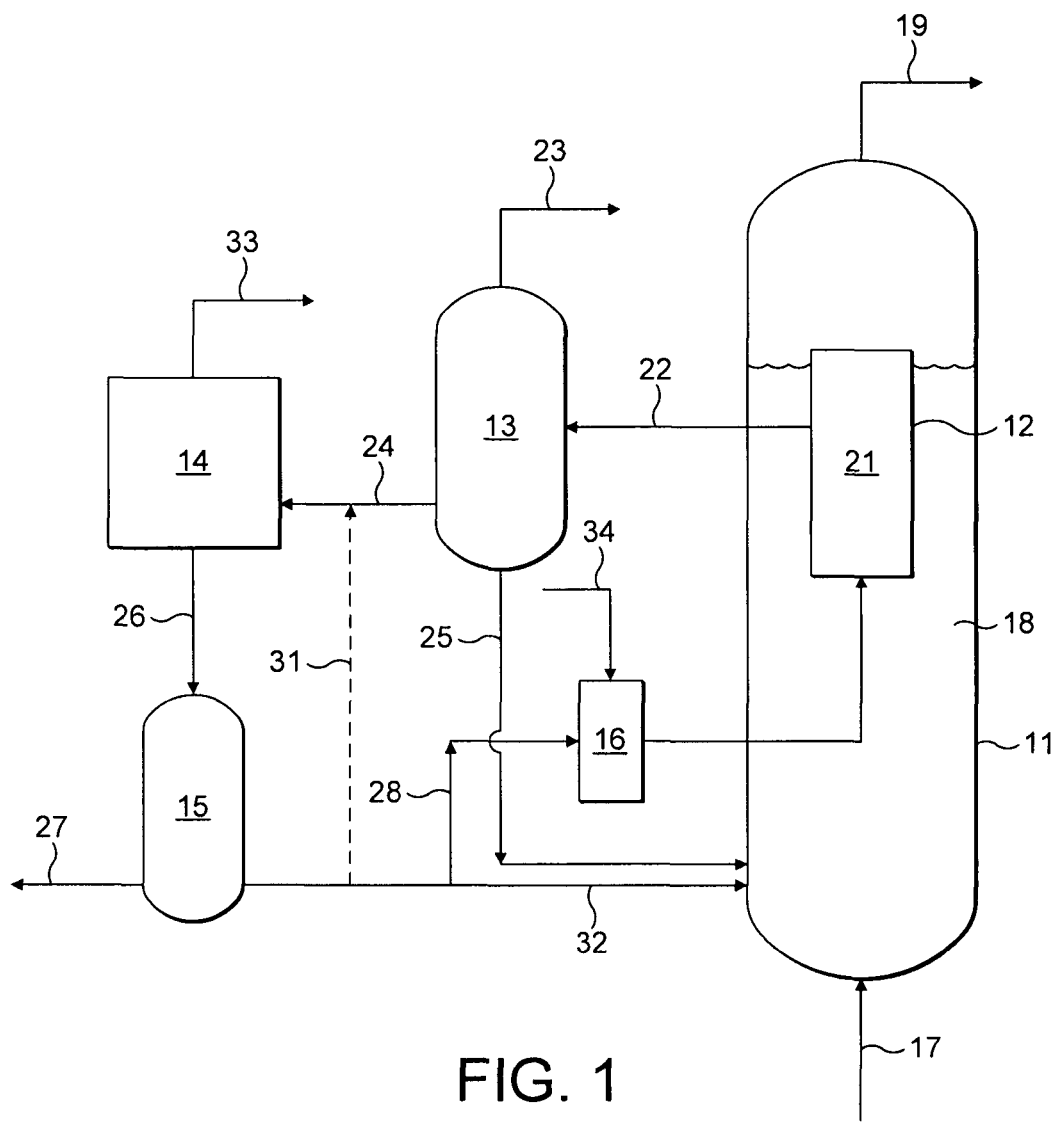
FIG. 1 is a schematic process diagram.
Figure 2:
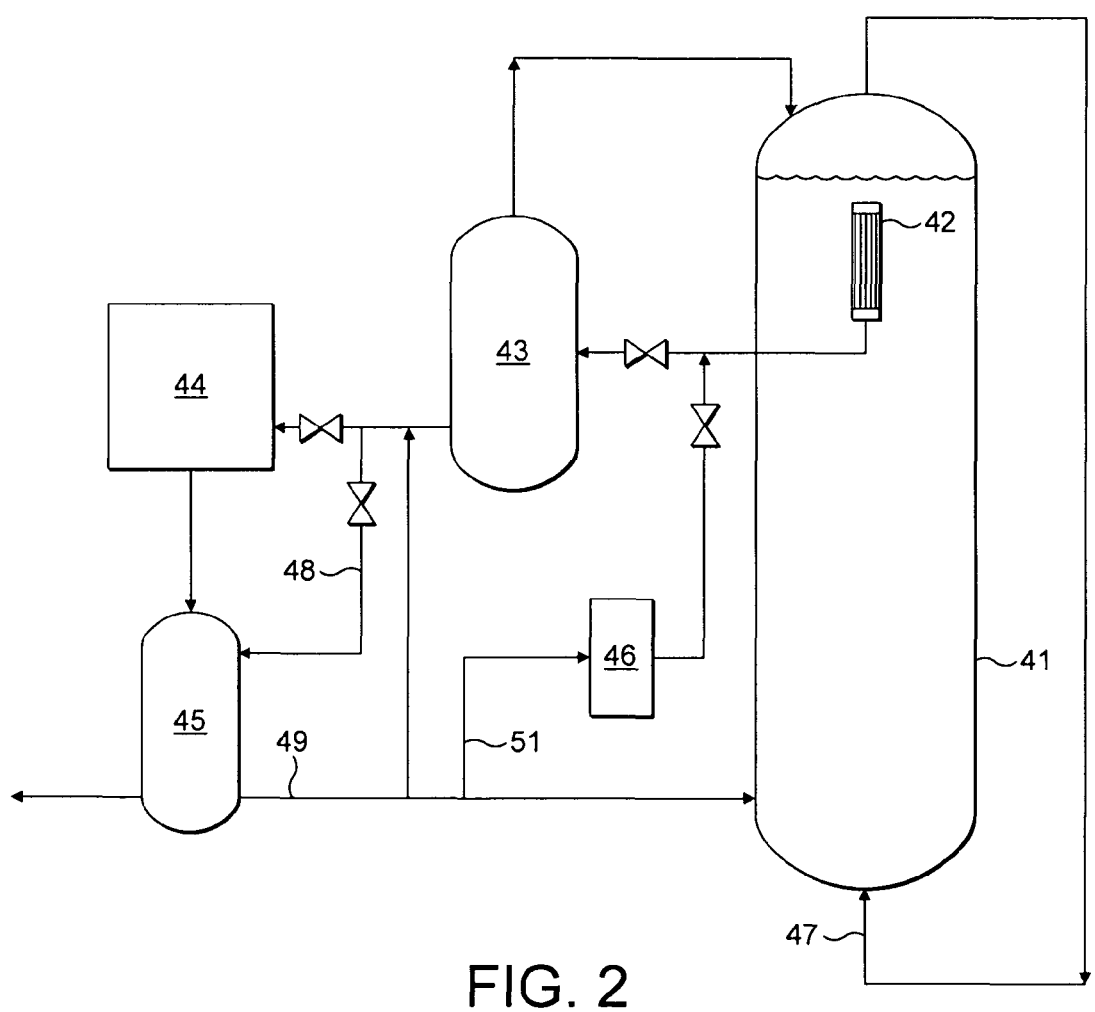
FIG. 2 is a schematic diagram of the apparatus used in the test examples.

FIG. 1 shows a process for carrying out a F-T synthesis reaction in accordance with the invention.

The apparatus comprises a slurry bubble column reactor 11, a primary filter unit 12 located within the reactor 11, a degasser unit 13, a wax polishing unit 14 outside the reactor 11, a wax buffer vessel 15 and a back flush vessel 16.

The reactor 11, is equipped with conventional internal features (not shown) such as heat exchange and gas distributor components (not shown). The internal filter 12 is relatively coarse, having a nominal opening size in the range +/−50% of catalyst mean particle size. The filters can either be of wedge wire type, woven mesh or any other suitable structured design.

The degasser 13 is a vessel in which gas entrained in the primary filtrate from the internal filter 12 is allowed to disengage. The pressure in the degasser is lower than on the outside of the primary filters to create the necessary driving force for the filtration. The wax polishing unit 14 is a secondary external filter, typically in the form of a cross flow filter or disposable filter cartridges. Alternatively, it could be a packed bed working as an adsorbent for the particles, a centrifuge or any other equipment able to remove fines from the liquid. It is arranged to remove particles, preferably >1 micron and more preferably ≥0.1 µm. These fine particles which are removed by the external filter are not recycled to the reactor and are normally disposed off.

The wax buffer 15 is a holding vessel for the final wax product from the wax polishing unit 14. The back flush vessel 16 is a holding vessel for the wax which is periodically flushed back through the internal filter 12.

The system operates in the following way. $H_2$ and CO gas is introduced into the reactor 11 via the reactant inlet 17. The gases enter a slurry 18 in the reactor comprising catalyst particles of mean particle size of 50 to 150 micron consisting of at least one active metal (Fe, Co) on a support suspended in liquid wax produced by the F-T synthesis reaction. The catalyst particles are at least partially maintained in suspension by the upwardly moving gas bubbles. Unreacted gases and lighter fractions are removed from the reactor 11 in a gas outlet line 19.

Wax product is separated out of the slurry 18 in the reactor 11 by the primary filter 12 and enters the filtrate zone 21 within the filter 12. This primary filtrate normally includes some catalyst fines. The primary filtrate is conveyed to the degasser unit 13, via a primary filtrate line 22, where entrained gas is disengaged and removed via a gas outlet line 23. The degassed primary filtrate is conveyed to the wax polishing unit 14 via a degassed filtrate line 24. A portion of the degassed primary filtrate can optionally be recycled directly to the reactor via a primary filtrate recycle line 25 for the purpose of returning relatively larger particles that have settled out in the degasser unit 13 to the reactor 11.

Catalyst fines are extracted from the degassed primary filtrate in the wax polishing unit 14 and then periodically or continuously removed from the wax polishing unit 14 via line 33. Polished wax product from the wax polishing unit 14 is conveyed to the wax buffer vessel 15 via wax product line 26. A portion of the wax product is removed as a final product via a product outlet line 27.

In addition, a portion of the product is conveyed to the back flush vessel 16 via a product back flush recycle line 28. Intermittently the wax product in the back flush vessel 16 is flushed back into the primary filter 12 via a back flush line 29. The backflush medium can alternatively be an other liquid fed to the backflush vessel 16 via a line 34 rather than the pure wax from the buffer vessel 15. A suitable liquid might be the condensed hydrocarbons from the overhead stream 19. The backflush 29 serves to clean the primary filter 12 and return catalyst particles from the outside of the primary filter to the slurry 18 in the reactor 11. Some or all of the wax in the buffer vessel 15 is recycled directly back to the reactor 11 via a recycle line 32.

The recycled product also serves to control the slurry level in the reactor and enables the rate of wax product removal from the reactor via the internal filter to be independent of the rate of net removal of product from the total system the latter being equal to the catalytic production of wax in the reactor.

The system also includes an option to divert some or all of the wax product from the buffer vessel 15 to the wax polishing unit 14 via a recycle divert line 31, prior to recycle lines 28 and 32.

EXAMPLE 1

The test apparatus consists of a column 41, a primary filter 42 in the column 41, a degasser 43, a disposable filter cartridge 44, a filtrate buffer vessel 45 and a backflush vessel 46.

The test apparatus is a column 41 with 20 cm ID and approx 3 m slurry level. The unit is operated at ambient temperature at pressures up to 7 bar using a hydrocarbon liquid with physical properties at ambient temperature resembling liquid wax at the operating temperature of an F-T reactor. Diethylbenzene sold under the trade name Therminol LT has been found to be a suitable model liquid. An alumina-supported cobalt-based FT-catalyst with mean particle size 70-80 microns was used. In this test, $N_2$ was used as feed gas 47 at an inlet superficial gas velocity of 16 cm/s at 7 bar pressure.

All of the filtrate from the filtrate buffer vessel 45 was recycled to the column 41 and via the recycle line 48 the filtrate could be secondary filtered through the disposable cartridge 44 when selected. When not selected, the primary filtrate passed via line 48 directly to the filtrate buffer vessel 45 and recycled to the column 41 via a line 49 and a portion used for backflushing of the primary filter 42 via line 51 and backflush vessel 46. The primary filter 42 used was a RigiMesh R from Pall Corporation and the secondary filter 44 used was a disposable filter from Europafilter called EF500HY able to remove particles >0.1 micron.

Figure 3:
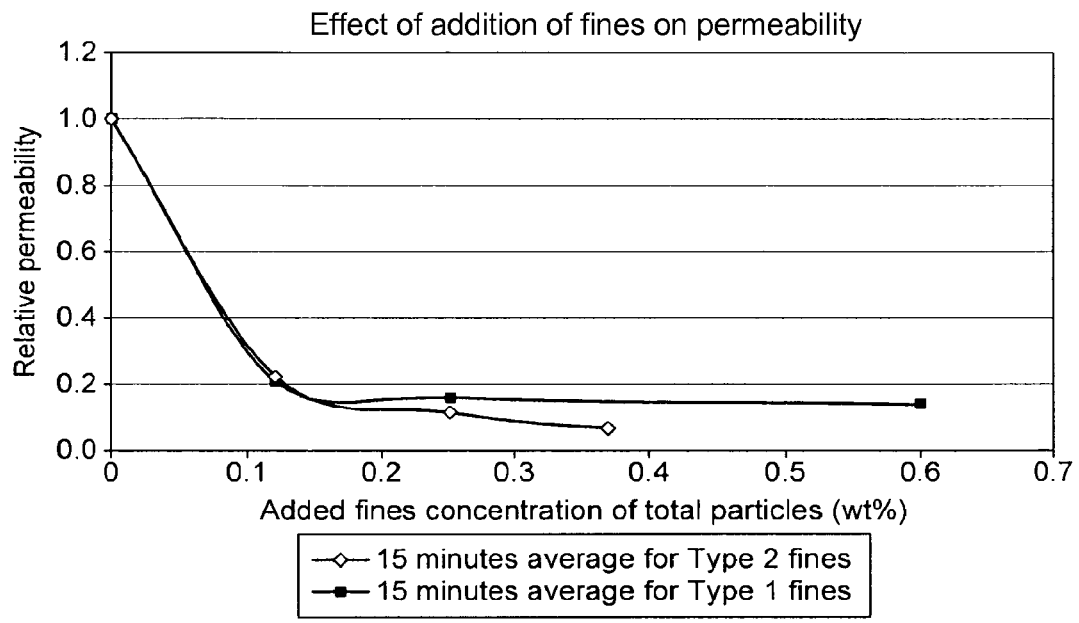
FIG. 3 is a graph showing the influence of fines content on the permeability.

In this example a substantially constant differential pressure (driving force) and backflush interval was applied to the primary filter 42 and the flow through the primary filter 42 was monitored. The sensitivity for 2 types of fines on the filtration permeability (flux/differential pressure) was measured by injecting a known amount of catalyst fines. Before addition of type 1 fines (arithmetic mean 8 micron, Sauter diameter 3.5 micron, 90 wt %<11 micron, 10 wt %<2 micron) the amount of fines<25 micron was below the detection limit (<0.05 wt %). By adding an amount of fines corresponding to 0.12 wt % of the total particle load in the column, the average permeability dropped by a factor>4 averaged over 15 min filtration time. For longer filtration cycles, the factor would be higher. Further addition of similar fines gave an additional, but much smaller decrease in the averaged permeability. The results are shown in FIG. 3.

The sensitivity for Type 2 fines (arithmetic mean particle size 23 micron, Sauter diameter 9.6 micron, 90 wt %<38 micron, 20 wt %<10 micron) on the filtration permeability (flux/differential pressure) was measured by injecting a known amount of catalyst fines. Before the addition, the amount of fines was below the detection limit (<0.05 wt %). By adding an amount of fines Type 2 corresponding to 0.12 wt % of the total particle load in the column, the average permeability dropped by a factor>4 averaged over 15 min filtration time. For longer filtration cycles, the factor would be higher. Further addition of similar fines gave an additional, but much smaller decrease in the averaged permeability. The results are again shown in FIG. 3.

Figure 4:
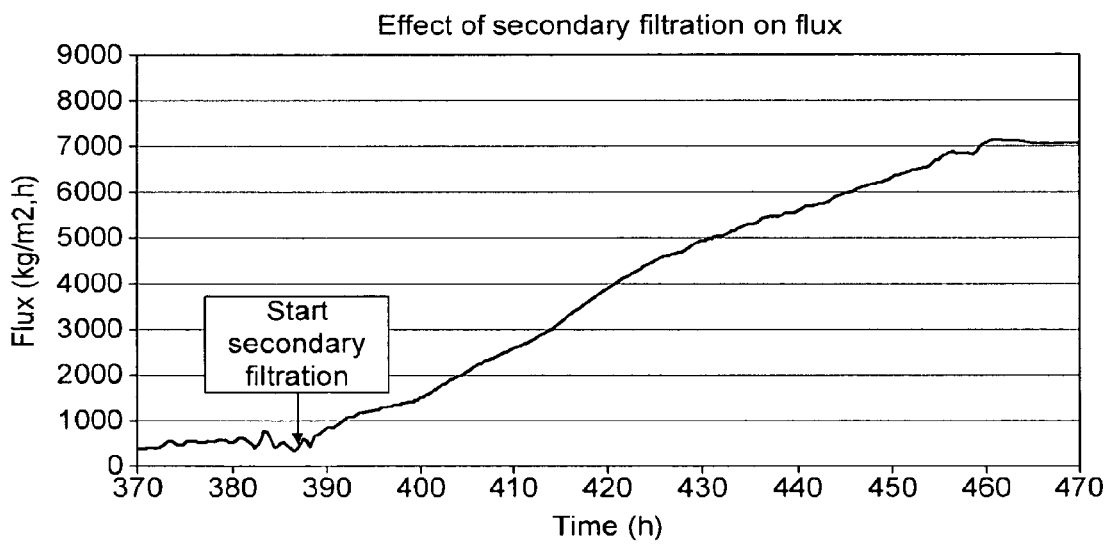
FIG. 4 is a graph showing the effect of removing fines in a secondary filter on the filtration flux in the primary filter.

By selecting secondary filtration of the primary filtrate before recycling to the column, the original filtration permeability could be recovered. The results are shown in FIG. 4. In FIG. 4 the primary filtration flux as function of time is given for the system after the addition of 0.3 wt % Type 1 fines and then starting secondary filtration.

From 380 h on the time axis, secondary filtration through the cartridge 44, was started and all the secondary filtrate recycled to the column 41. The secondary filtration step 44 had a high efficiency for removing particles>0.1 micron. During the next 70 h, the flux through the primary filter system 42 increased from 500 to 7000 kg/m²h. This shows a significant advantage from removing fines by recycling pure (catalyst free) filtrate at a high rate to the slurry reactor, thereby effectively purging catalyst fines from the reactor slurry.

In an industrial plant, several or all primary filter units may be hooked up to one filtrate cleaning unit and back-flushing of individual primary filter units could be achieved by being connected to the cleaned liquid product recycle line from the filtrate cleaning unit through a system of controlling valves.

The invention claimed is:

1. Apparatus for conducting a three-phase reaction, in which gaseous reactants are reacted in the presence of a finely divided solid catalyst in suspension in a liquid comprising, at least in part, the reaction product of the gaseous reactants, thereby forming a slurry, the apparatus comprising a reactor vessel, a primary filter unit, a filtrate cleaning unit, a degasser unit, and a filtrate buffer unit, and in which: the reactor vessel includes a reactant inlet and a gas outlet and is arranged to contain the slurry in use; the primary filter unit is arranged to be in contact with slurry in use, the primary filter unit having an outlet for primary filtrate; the filtrate cleaning unit is arranged to remove further particulate material from the filtrate in use, and includes an inlet for the filtrate, an outlet for liquid product that has been subjected to cleaning; the degasser unit is located between the primary filter unit and the filtrate cleaning unit; and the filtrate buffer unit is arranged to receive cleaned liquid product from the filtrate cleaning unit, the filtrate buffer unit having liquid product outlet, a liquid product recycle line from the filtrate buffer unit directly to the reactor vessel which conveys the liquid product from the filtrate buffer unit directly into the reactor vessel without passing through the primary filter unit, and an optional liquid product recycle line to the primary filter unit.

2. Apparatus as claimed in claim 1, further including a cleaned liquid product recycle line from the filtrate cleaning unit to the primary filter unit, whereby the primary filter can be back flushed using a portion of the liquid product.

3. Apparatus as claimed in claim 1, in which the primary filter is located within the reactor vessel.

4. Apparatus as claimed in claim 3, in which the primary filter is arranged, in use, to be at least partially immersed in the slurry.

5. Apparatus as claimed in claim 1, in which the filtrate cleaning unit is outside the reactor vessel.

6. Apparatus as claimed in claim 1, in which the filtrate cleaning unit is a secondary filter unit, the primary filter unit comprising a relatively coarse filter and the secondary filter unit comprising a relatively fine filter.

7. Apparatus as claimed in claim 1, in which the degasser unit includes a gas outlet, an outlet for filtrate leading to the filtrate cleaning unit, and an optional recycle line for filtrate leading back to the reactor vessel.

8. Apparatus as claimed in claim 1, further including a recycle line from the filtrate buffer unit to the filtrate cleaning unit.

9. A process for conducting a three phase reaction in the apparatus according to claim 1, in which gaseous reactants are reacted in the presence of a finely divided solid catalyst in a suspension in a liquid comprising, at least in part, the reaction product of the gaseous reactants, thereby forming a slurry, the process comprising the steps of:
 introducing the gaseous reactants into the slurry in the reactor vessel;
 subjecting the slurry to a filtration step to remove particulate material in the primary filter unit to produce a filtrate stream;
 subjecting the filtrate stream to a cleaning step in the filtrate cleaning unit thereby removing further particulate material to produce a liquid product stream to be received in the filtrate buffer unit; and
 recycling at least a portion of the liquid product stream from the filtrate buffer unit to the reactor vessel by conveying the liquid product stream from the filtrate buffer unit directly into the reactor vessel without passing through the primary filter unit, and from the filtrate buffer unit to the filtrate cleaning unit.

10. A process as claimed in claim 9, including the further step of recycling at least a portion of the liquid product stream to the primary filter, thereby back flushing the primary filter.

11. A process as claimed in claim 10, in which the back flushing causes catalyst particles located on the primary filter to re-enter the slurry.

12. A process as claimed in claim 9, further including a fines removal step in which fine catalyst particles filtered out in the cleaning step are removed from the filtrate cleaning unit.

13. A process as claimed in claim 9, further including a degassing step in the degasser unit in which gas is separated from the filtrate stream from the primary filter unit and is removed from the process, while the remaining, liquid phase is directed to the filtrate cleaning unit.

14. A process as claimed in claim 13, in which a portion of the liquid phase from the degassing step is recycled to the reactor vessel.

15. A process as claimed in claim 9, for producing hydrocarbons in which the reaction is a Fischer-Tropsch synthesis reaction, carried out in the reactor vessel, wherein the reactor vessel comprises a slurry bubble column reactor, and in which $H_2$ and CO are supplied to the slurry in the reactor, the slurry comprising the catalyst in suspension in the liquid including the reaction products of the $H_2$ and CO, the catalyst being maintained in suspension in the slurry at least partly by the motion of the gas supplied to the slurry.

16. A process as claimed in claim 15, in which the reaction temperature is in the range 190-250° C. and/or the reaction pressure is in the range 10-60 bar.

17. A process as claimed in claim 15, in which a $H_2$/CO ratio of the gases supplied to the Fischer-Tropsch synthesis reactor is in the range 1.1 to 2.2.

18. A process as claimed in claim 15, in which the superficial gas velocity in the reactor is in the range 5 to 60 cm/s.

19. A process as claimed in claim 15, in which the product of the Fischer-Tropsch synthesis reaction is subsequently subjected to post-processing.

20. A process as claimed in claim 19, in which the post-processing is selected from de-waxing, hydro-isomerisation, hydro-cracking and combinations of these.

* * * * *